United States Patent
Kramer et al.

(10) Patent No.: US 8,802,731 B2
(45) Date of Patent: Aug. 12, 2014

(54) N-ACETYL BETA ALANINE METHODS OF USE

(75) Inventors: Ronald Kramer, Phoenix, AZ (US); Alexander Nikolaidis, New Kallikratia (GR)

(73) Assignee: ThermoLife International, LLC, Phoenix, AZ (US)

( * ) Notice: Subject to any disclaimer, the term of this patent is extended or adjusted under 35 U.S.C. 154(b) by 61 days.

(21) Appl. No.: 13/446,416

(22) Filed: Apr. 13, 2012

(65) Prior Publication Data

US 2012/0264826 A1     Oct. 18, 2012

Related U.S. Application Data

(60) Provisional application No. 61/475,179, filed on Apr. 13, 2011.

(51) Int. Cl.
| | | |
|---|---|---|
| *A01N 37/12* | (2006.01) | |
| *A01N 37/44* | (2006.01) | |
| *A61K 31/195* | (2006.01) | |
| *C07C 233/00* | (2006.01) | |
| *C07C 235/00* | (2006.01) | |
| *C07C 237/00* | (2006.01) | |
| *C07C 239/00* | (2006.01) | |
| *A61K 31/197* | (2006.01) | |

(52) U.S. Cl.
CPC .................................. *A61K 31/197* (2013.01)
USPC .......................................... 514/563; 564/193

(58) Field of Classification Search
USPC .......................................... 514/563; 564/193
See application file for complete search history.

(56) References Cited

U.S. PATENT DOCUMENTS

2006/0063827 A1\*   3/2006   Yu et al. ........................ 514/423

OTHER PUBLICATIONS

Artioli et al. "Role of beta-Alanine Supplementation on Muscle Carnosine and Exercise Performance" Med. Sci. Sprots Exerc, Jun. 2010, vol. 42, No. 6, pp. 1162-1173.\*

\* cited by examiner

*Primary Examiner* — Kendra D Carter
(74) *Attorney, Agent, or Firm* — Booth Udall Fuller, PLC

(57) ABSTRACT

Methods for increasing athletic performance, preventing paresthesia, increasing beta alanine absorption and cell membrane permeability through both passive diffusion and active transport, and increasing the half-life of beta alanine present in a blood stream in a human or animal are disclosed. Each method includes administering to the human or animal a pharmaceutically effective amount of N-Acetyl Beta Alanine or an N-Acetyl Beta Alanine composition.

1 Claim, No Drawings

N-ACETYL BETA ALANINE METHODS OF USE

CROSS REFERENCE TO RELATED APPLICATION

This application claims the benefit of the filing date of U.S. Provisional Patent Application 61/475,179 entitled "N-Acetyl Beta Alanine Methods of Use", filed on Apr. 13, 2011, the disclosure of which being hereby incorporated entirely herein by reference.

BACKGROUND

1. Technical Field

Aspects of this document relate generally to n-acetyl beta alanine and methods of use.

2. Background

β-Alanine (or beta-alanine) is a naturally occurring beta amino acid, which are amino acids in which the amino group is at the β-position from the carboxylate group. Its structure is as follows:

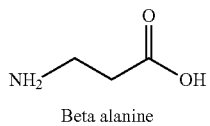

Beta alanine

β-Alanine is not used in the biosynthesis of any major proteins or enzymes. It is formed in vivo by the degradation of dihydrouracil and carnosine. It is a component of the naturally occurring peptides carnosine and anserine and also of pantothenic acid (vitamin B5) which itself is a component of coenzyme A. Under normal conditions, β-alanine is metabolized into acetic acid.

β-Alanine is the rate-limiting precursor of carnosine, which is to say carnosine levels are limited by the amount of available β-Alanine. Carnosine removes excess acid from the muscle cell, thus reducing fatigue, etc. Therefore, the beneficial effects described for beta-alanine also apply to carnosine. Supplementation with β-alanine has been shown to increase the concentration of carnosine in muscles, decrease fatigue in athletes and increase total muscular work done.

See for example the following publications. In "Muscle carnosine metabolism and beta-alanine supplementation in relation to exercise and training", Derave et al., Sports Med. 2010 Mar. 1; 40(3):247-63, the researchers have made an extensive review of beta-alanine's physiological role, it's effects and it's ability to enhance sports performance. In "The effects of 10 weeks of resistance training combined with beta-alanine supplementation on whole body strength, force production, muscular endurance and body composition", Kendrick et al., Amino Acids. 2008 May; 34(4):547-54 it was exhibited that beta alanine supplementation can enhance muscle carnosine levels. In "Beta-alanine supplementation reduces acidosis but not oxygen uptake response during high-intensity cycling exercise", Baquet et al., Eur J Appl Physiol. 2010 February; 108(3):495-503, it was described that beta alanine supplementation at 4.8 grams per day can attenuate acidosis due to exercise, resulting in increased performance in some models.

β-Alanine, therefore, finds great use in sports supplements to reduce muscle fatigue, muscle damage, promote endurance, promote recovery, increase strength and improve athletic performance and body composition. Apart from these uses beta-alanine may be used for the treatment of muscle wasting diseases, in anti-aging formulas, in overall health formulas and any other use where increased muscular performance is wanted. The effective doses used in studies range from 2.4 grams per day (see for example, "The effect of beta-alanine supplementation on neuromuscular fatigue in elderly (55-92 Years): a double-blind randomized study", Stout et al., Journal of the International Society of Sports Nutrition 2008, 5:21, where supplementation of 800 mg×3 per day resulted in 28% increase in physical working capacity fatigue threshold) to as much as 6 grams per day, although it is not uncommon to see supplements with lower (as little as 500 mg) or larger doses.

Despite the foregoing, beta alanine's use still suffers from drawbacks. The biggest drawback of beta alanine use is paresthesia, a "tingling" sensation users experience that comes from reaction of beta alanine with nerves of the skin. Symptoms of paresthesia start at doses as low as 800 mg (see, for example, "Role of beta-alanine supplementation on muscle carnosine and exercise performance", Artioli et al., Med Sci Sports Exerc. 2010 June; 42(6):1162-73, where it is mentioned that "Symptoms of paresthesia may be observed if a single dose higher than 800 mg is ingested") and can worsen with higher doses. This is so uncomfortable to some users that they opt to use beta alanine in many small servings during the day or just not all.

Another drawback of beta alanine is that while it is water soluble, it is very poorly soluble in organic solvents. Beta alanine is described to have a water solubility of 55-89 grams/100 ml. This makes it extremely hydrophilic and lipophobic, which may hinder it's capacity to bypass certain cell membranes like the blood-brain barrier (see, for example, "Determination of lipophilicity and its use as a predictor of blood-brain barrier penetration of molecular imaging agents", Waterhouse, Mol Imaging Biol. 2003 November-December; 5(6):376-89, where it is described how increasing lipophilicity increases blood-brain barrier permeation) or the muscle cell wall by passive diffusion. Although beta alanine is transported by an active transport system (see, for example, "Sodium and chloride ion-dependent transport of beta-alanine across the blood-brain barrier", Komura et al., J. Neurochem. 1996 July; 67(1):330-5, where Komura et. al. describe how beta-alanine can be transported via the Blood Brain Barrier by a sodium/chloride dependent channel) it would be desirable to increase absorption rate by adding passive diffusion to the absorption mechanisms (increasing lipophilicity can increase permeation and absorption through biological membranes).

SUMMARY

In one aspect, a method for increasing athletic performance in a human or animal is disclosed. The method includes administering to the human or animal a pharmaceutically effective amount of N-Acetyl Beta Alanine.

In another aspect, a method for preventing paresthesia in a human or animal is disclosed. The method includes administering to the human or animal a pharmaceutically effective amount of N-Acetyl Beta Alanine.

In still another aspect, a method for increasing beta alanine absorption and cell membrane permeability through both passive diffusion and active transport in a human or animal is disclosed. The method includes administering to the human or animal a pharmaceutically effective amount of N-Acetyl Beta Alanine.

In yet another aspect, a method for increasing the half-life of beta alanine present in a blood stream in a human or animal is disclosed. The method includes administering to the human or animal a pharmaceutically effective amount of N-Acetyl Beta Alanine.

Implementations may comprise one or more of the following.

The methods may include administering a pharmaceutically effective amount of an N-Acetyl Beta Alanine composition including N-Acetyl Beta Alanine and a pharmaceutically acceptable additive. The additive may be a carrier, excipient, binder, colorant, flavoring agent, preservative, buffer, dilutant, or any combination thereof.

N-Acetyl Beta Alanine or N-Acetyl Beta Alanine composition may be in the form of a capsule, tablet, pill, liquid, liquid suspension, vapor, gas, powder, granulate or pulverulence.

Advantages of administering an N-acetyl beta alanine alone or as part of a Composition are:

Elimination of the paresthesia side-effect that is typically present in administration of beta alanine without the inconvenience and added cost of devising multiple small dose regimes or time-released forms that have been suggested in the past.

Higher lipophylicity without eliminating water-solubility, therefore, asserting greater absorption and cell membrane permeability through both passive diffusion and active transport.

Greater half life of beta alanine.

Totally improved effectiveness and ease of use compared to beta alanine.

The foregoing and other aspects, features, and advantages will be apparent to those artisans of ordinary skill in the art from the DESCRIPTION, and from the CLAIMS.

DESCRIPTION

Overview, Terminology and Definitions

In describing implementations of an N-acetyl beta alanine compounds or compositions and methods of use, the following terminology will be used in accordance with the definitions and explanations set out below. Notwithstanding, other terminology, definitions, and explanations may be found throughout this document, as well.

As used herein, "Composition" is a term used in its broadest sense and may refer to a mixture of constituent substances or ingredients. "Mixture" is a term used in its broadest sense and may refer to two or more constituent substances or ingredients (chemical species present in a system) which have been combined (not necessarily in fixed proportions and not necessarily with chemical bonding and not necessarily so that each substance retains its own chemical identity). Mixtures can be the product of a blending or mixing of chemical substances like elements and compounds, without chemical bonding or other chemical change, so that each ingredient substance retains its own chemical properties and makeup. Mixtures can be either homogeneous or heterogeneous. A homogeneous mixture is a type of mixture in which the composition is uniform. A heterogeneous mixture is a type of mixture in which the composition can easily be identified, as there are two or more phases present. A homogeneous mixture in which there is both a solute and solvent present is also a solution.

A "Compound" is a term used in its broadest sense and may refer to a chemical substance comprising two or more different chemically bonded chemical constituent elements or ingredients, with a fixed ratio or proportion by weight. The atoms within a compound can be held together by a variety of interactions, ranging from covalent bonds to electrostatic forces in ionic bonds. The physical and chemical properties of compounds are different from those of their constituent elements. This is one of the main criteria for distinguishing a compound from a mixture of elements or other substances because a mixture's properties are generally closely related to and dependent on the properties of its constituents. However, some mixtures are so intimately combined that they have some properties similar to compounds. Another criterion for distinguishing a compound from a mixture is that the constituents of a mixture can usually be separated by simple, mechanical means such as filtering, evaporation, or use of a magnetic force, but the components of a compound can only be separated by a chemical reaction. Conversely, mixtures can be created by mechanical means alone, but a compound can only be created (either from elements or from other compounds, or a combination of the two) by a chemical reaction.

Thus, for purposes of this disclosure, "Composition" may refer to a mixture of at least N-acetyl beta alanine in combination with some other component or constituent.

As used herein, "N-acetyl beta alanine" is a term used in its broadest sense and may refer to 3-acetamidopropanoic acid, N-Acetyl-beta-alanine, 3-acetamidopropanoic acid, and 3-(acetylamino)propanoic acid. It has a molecular formula of $C_5H_9NO_3$ and a moleculr weight of 131.129860 [g/mol]. It appears as a white fine powder and is odorless and soluble in water and organic solvents.

It also may refer to its many different chemical forms including its physiologically active salts or esters or chelates, its combinations with its various salts, its tautomeric, polymeric and/or isomeric forms, its analog forms, and/or its derivative forms.

It also may refer to other amides of beta alanine. An example would be N-butyl beta-alanine or N-isopropyl beta alanine. Furthermore after the acetylation has taken place, further modifications of the molecule could take place, like etherification of the carboxylic group wielding for example n-acetyl beta-alanine ethyl-ester or n-acetyl beta-alanine methyl ester. Another modification would be the use of different salts of the acetylated beta alanine, like n-acetyl beta alanine nitrate, Sodium n-acetyl beta alanine, etc.

For the exemplary purposes of this disclosure, the structure of N-acetyl beta alanine and some of the other chemical forms mentioned above are shown below:

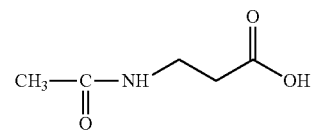

N-acetyl beta alanine

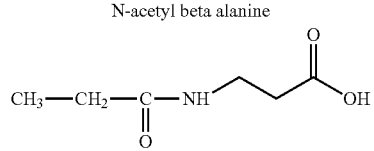

N-Propionyl beta alanine

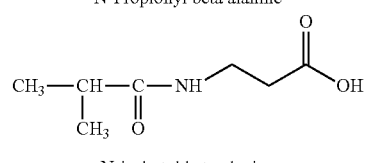

N-isobutyl beta alanine

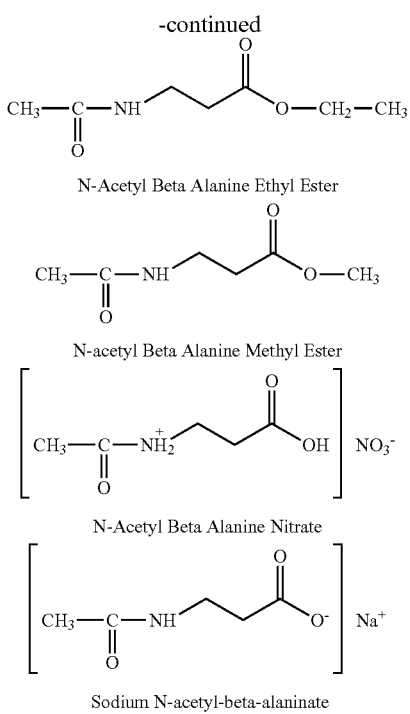

N-Acetyl Beta Alanine Ethyl Ester

N-acetyl Beta Alanine Methyl Ester

N-Acetyl Beta Alanine Nitrate

Sodium N-acetyl-beta-alaninate

As used herein, "pharmaceutically acceptable additive" or "additive" are terms used in their broadest sense. Particular implementations of the compositions described in this document may also comprise an additive (e.g. one of a solubilizer, an enzyme inhibiting agent, an anticoagulant, an antifoaming agent, an antioxidant, a coloring agent, a coolant, a cryoprotectant, a hydrogen bonding agent, a flavoring agent, a plasticizer, a preservative, a sweetener, a thickener, and combinations thereof) and/or a carrier (e.g. one of an excipient, a lubricant, a binder, a disintegrator, a diluent, an extender, a solvent, a suspending agent, a dissolution aid, an isotonization agent, a buffering agent, a soothing agent, an amphipathic lipid delivery system, and combinations thereof). These additives may be solids or liquids, and the type of additive may be generally chosen based on the type of administration being used. Those of ordinary skill in the art will be able to readily select suitable pharmaceutically effective additives from the disclosure in this document. In particular implementations, pharmaceutically acceptable additives may include, by non-limiting example, calcium phosphate, cellulose, stearic acid, croscarmelose cellulose, magnesium stearate, and silicon dioxide.

As used in this document, "pharmaceutically effective" is a phrase used in its broadest sense, including, by non-limiting example, effective in a clinical trial, for a specific patient, or only placebo-effective.

As used in this document, "Pharmaceutically acceptable" is a phrase used in its broadest sense and may describe ingredients of a pharmaceutical composition that meet Food and Drug Administration (FDA) standards, United States Pharmacopeial Standards (USP), US Department of Agriculture (USDA) standards for food-grade materials, commonly accepted standards of the nutritional supplement industry, industry standards, botanical standards, or standards established by any individual. These standards may delineate acceptable ranges of aspects of ingredients of a pharmaceutical composition such as edibility, toxicity, pharmacological effect, or any other aspect of a chemical, composition, or preparation used in implementations of a pharmaceutical composition.

Components/Compounds/Compositions

N-acetyl beta alanine is an existing naturally occurring beta-alanine analog that has not been administered in humans for enhancing athletic performance or any other purpose for which beta-alanine is used.

In the body, N-acetyl beta alanine is de-acetylated by the enzyme N-acetyl beta alanine deacetylase. N-acetyl-beta-alanine deacetylase (ENZYME entry: EC 3.5.1.21) is an enzyme that catalyzes the chemical reaction: N-acetyl-beta-alanine+ $H_2O \rightleftharpoons$ acetate+beta-alanine. Thus, the two substrates of this enzyme are N-acetyl-beta-alanine and $H_2O$, whereas its two products are acetate and beta-alanine. This enzyme belongs to the family of hydrolases, those acting on carbon-nitrogen bonds other than peptide bonds, specifically in linear amides. The systematic name of this enzyme class is N-acetyl-beta-alanine amidohydrolase. This enzyme participates in beta-alanine metabolism.

Even though N-acetyl-beta-alanine and beta alanine have some similar structure, there is evidence showing there is no reasonable expectation of similar properties. As evidence that N-acetyl beta alanine is not an equally functioning beta alanine analog (but rather a higher functioning one), when compared to other beta alanine forms, N-acetyl beta alanine offers very different properties, such as improved cell permeability, longer half-life and more importantly no paresthesia observed even at large doses of 5+ grams. N-acetyl-beta-alanine was found by applicants to possess a solubility in water of 22 g/100 mg—enough for all practical purposes—but yet less hydrophilic than beta alanine.

The N-acetyl form of beta alanine cannot react with nerve ends to produce paresthesia since amides are neurologically inactive. Therefore, by slowly converting to beta-alanine through deacetylation, paresthesia is prevented due to low but constant blood-serum beta alanine concentrations. This also increases the half-life of beta-alanine present in the blood stream and cell membrane permeability.

Thus, advantages of administering an N-acetyl beta alanine alone or as part of a Composition are:

Elimination of the paresthesia side-effect that is typically present in administration of beta alanine without the inconvenience and added cost of devising multiple small dose regimes or time-released forms that have been suggested in the past.

Higher lipophylicity without eliminating water-solubility, therefore, asserting greater absorption and cell membrane permeability through both passive diffusion and active transport.

Greater half life of beta alanine.

Totally improved effectiveness and ease of use compared to beta alanine.

For the exemplary purposes of this disclosure, N-acetyl beta alanine could be used either as a nutritional supplement or a pharmaceutical composition.

An exemplary composition of N-acetyl beta alanine to enhance performance in athletes (in powder form to be mixed with water and drunk once per day, preferably before training on training days) is: N-acetyl-beta-alanine 6 grams; Creatine Nitrate 5 grams; and Vitamin C 300 mg.

An exemplary composition containing N-acetyl beta alanine to prevent neuronal damage in diabetics is: Ascorbic Acid 200 mg; Alpha Lipoic Acid 100 mg; N-acetyl-Beta-Alanine 3 grams; and Vitamin E (as gamma tocopherol) 10.000 IU.

An exemplary composition containing N-acetyl beta alanine to be used as an antiaging supplement is: Resveratrol 300 mg; Piperine 10 mg; N-acetyl-beta alanine 2 grams; and Ecdysterone 200 mg.

Manufacture

Implementations of N-acetyl beta alanine Compounds or Compositions may be synthesized or created in a wide variety of manners, and may be made from a wide variety of materials. Those of ordinary skill in the art will readily be able to select appropriate materials and methods to manufacture and use the compounds and compositions disclosed herein.

Accordingly, although there are a variety of method implementations for producing pharmaceutical compositions, for the exemplary purposes of this disclosure, a method implementation for producing an N-acetyl beta alanine may include the reaction of isomolar quantities of beta-alanine and Acetyl chloride in aqueous solution or any other polar, easily evaporated solvent such as methanol, alcohol, pyridine, and the like. Catalysts such as triethylamine, pyridine or DMAP can be used to speed up the reaction while as bases they can be used to neutralize the produced hydrochloric acid. The mixture may be stirred for one hour and the solvent is thereafter dried under vacuum to provide n-acetyl beta alanine.

The reaction proceeds as follows: $CH_3COCl + 2HN—CH_2-CH_2-COOH \rightarrow Ch_3CONH—CH_2-CH_2-COOH + HCl$ Additional pharmaceutically acceptable additives or inert ingredients can also be added, and then the pharmaceutical composition can be separated into discrete quantities for distribution and/or administration.

Measuring specific quantities of N-acetyl beta alanine, water or solvent, and pharmaceutically acceptable additives or inert ingredients, may involve any number of steps and implementing components, and measuring specific quantities of N-acetyl beta alanine, water or solvent, and pharmaceutically acceptable additives or inert ingredients, may be accomplished readily from this disclosure. For the exemplary purposes of this disclosure, measuring specific quantities of N-acetyl beta alanine, water or solvent, and pharmaceutically acceptable additives or inert ingredients, may comprise using a scale, a solid or liquid dispensing apparatus, or other measurement device capable of measuring solid mass or liquid volume to produce a desired quantity of N-acetyl beta alanine, water or solvent, and pharmaceutically acceptable ingredient.

It should be appreciated that any of the components of particular implementations of an N-acetyl beta alanine Compound or Composition may be used as supplied commercially, or may be preprocessed by, by non-limiting example, any of the methods and techniques of agglomeration, air suspension chilling, air suspension drying, balling, coacervation, comminution, compression, pelletization, cryopelletization, extrusion, granulation, homogenization, inclusion Compoundation, lyophilization, melting, mixed, molding, pan coating, solvent dehydration, sonication, spheronization, spray chilling, spray congealing, spray drying, or other processes known in the art depending in part on the dosage form desired. The various components may also be pre-coated or encapsulated as known in the art. It will also be clear to one of ordinary skill in the art that appropriate additives may also be introduced to the composition or during the processes to facilitate the preparation of the dosage forms, depending on the need of the individual process.

Mixing the measured quantities of N-acetyl beta alanine, water or solvent, and pharmaceutically acceptable additives or inert ingredients for Compounds, or mixing the measured quantities of N-acetyl beta alanine, and pharmaceutically acceptable additives or inert ingredients for Compositions, may involve any number of steps and implementing components, and may be accomplished readily from this disclosure.

For the exemplary purposes of this disclosure, mixing the measured quantities of N-acetyl beta alanine, water or solvent, and pharmaceutically acceptable additives or inert ingredients, may comprise combining the measured quantities of m N-acetyl beta alanine, water or solvent, and pharmaceutically acceptable additives or inert ingredients, under the influence of physical, ultrasonic, or electrostatic forces to create a desired degree of intermingling and/or chemical reaction of the N-acetyl beta alanine, water or solvent and any pharmaceutically acceptable ingredients. The mixed may be accomplished when the N-acetyl beta alanine, water or solvent and/or any pharmaceutically acceptable ingredients are in a solid, liquid, or semisolid state.

Separating the N-acetyl beta alanine Compound or Composition into discrete quantities for distribution may involve any number of steps and implementing components, and separating the N-acetyl beta alanine Compound or Composition into discrete quantities for distribution may be accomplished readily from this disclosure. For the exemplary purposes of this disclosure, separating the N-acetyl beta alanine Compound or Composition into discrete quantities for distribution may involve utilizing a specific piece of equipment, for example, a conventional tablet forming apparatus to shape the formed composition into individual tablets, each containing a desired dose of N-acetyl beta alanine Compound or Composition. The separating process may be accomplished when the N-acetyl beta alanine Compound or Composition is in a solid, liquid, or semisolid state.

Those of ordinary skill in the art will be able to readily select manufacturing equipment and pharmaceutically acceptable additives or inert ingredients to manufacture implementations of an N-acetyl beta alanine Compound or Composition. For the exemplary purposes of this disclosure, some examples of pharmaceutically acceptable additives or inert ingredients and manufacturing process are included below, particularly those that relate to manufacture of implementations of an N-acetyl beta alanine Compound or Composition in tablet form. Notwithstanding the specific examples given, it will be understood that those of ordinary skill in the art will readily appreciate how to manufacture implementations of an N-acetyl beta alanine Compound or Composition according to the other methods of administration and delivery disclosed in this document.

Accordingly, compounds and Compositions may include a acceptable additive (e.g. one of a solubilizer, an enzyme inhibiting agent, an anticoagulant, an antifoaming agent, an antioxidant, a coloring agent, a coolant, a cryoprotectant, a hydrogen bonding agent, a flavoring agent, a plasticizer, a preservative, a sweetener, a thickener, and combinations thereof) and/or a acceptable carrier (e.g. one of an excipient, a lubricant, a binder, a disintegrator, a diluent, an extender, a solvent, a suspending agent, a dissolution aid, an isotonization agent, a buffering agent, a soothing agent, an amphipathic lipid delivery system, and combinations thereof).

For example, a particular implementation of an N-acetyl beta alanine Compound or Composition may include a lubricant. Lubricants are any anti-sticking agents, glidants, flow promoters, and the like materials that perform a number of functions in tablet manufacture, for example, such as improving the rate of flow of the tablet granulation, preventing adhesion of the tablet material to the surface of the dies and punches, reducing interparticle friction, and facilitating the ejection of the tablets from the die cavity. Lubricants may comprise, for example, magnesium stearate, calcium stearate, talc, and colloidal silica.

Particular implementations of an N-acetyl beta alanine Compound or Composition may also include a binder. Binders are any agents used to impart cohesive qualities to powdered material through particle-particle bonding. Binders may include, for example, matrix binders (e.g. dry starch, dry sugars), film binders (e.g. celluloses, bentonite, sucrose), and chemical binders (e.g. polymeric cellulose derivatives, such as methyl cellulose, carboxy methyl cellulose, and hydroxy propyl cellulose); and other sugar, gelatin, non-cellulosic binders and the like.

Disintegrators may be used in particular implementations of an N-acetyl beta alanine Compound or Composition to facilitate the breakup or disintegration of tablets after administration. Disintegrators may include, for example, starch, starch derivatives, clays (e.g. bentonite), algins, gums (e.g. guar gum), cellulose, cellulose derivatives (e.g. methyl cellulose, carboxymethyl cellulose), croscarmellose sodium, croscarmellose cellulose, and other organic and inorganic materials.

Implementations of an N-acetyl beta alanine Compound or Composition may include diluents, or any inert substances added to increase the bulk of the N-acetyl beta alanine Compound to make a tablet a practical size for compression. Diluents may include, for example, calcium phosphate, calcium sulfate, lactose, mannitol, magnesium stearate, potassium chloride, and citric acid, among other organic and inorganic materials.

Buffering agents may be included in an N-acetyl beta alanine Compound or Composition and may be any one of an acid and a base, where the acid is, for example, propionic acid, p-toluenesulfonic acid, salicylic acid, stearic acid, succinic acid, tannic acid, tartaric acid, thioglycolic acid, or toluenesulfonic acid, and the base is, for example, ammonium hydroxide, potassium hydroxide, sodium hydroxide, sodium hydrogen carbonate, aluminum hydroxide, calcium carbonate, and other organic and inorganic chemicals.

With respect to delivery of particular implementations of an N-acetyl beta alanine Compound or Composition, for the exemplary purposes of this disclosure, tablets may be utilized. Tablets are any solid pharmaceutical dosage form containing a pharmaceutically acceptable active agent or agents to be administered with or without suitable pharmaceutically acceptable additives and prepared either by compression or molding methods well known in the art. Tablets have been in widespread use and remain popular as a dosage form because of the advantages afforded both to the manufacturer (e.g., simplicity and economy of preparation, stability, and convenience in packaging, shipping, and dispensing) and the patient (e.g., accuracy of dosage, compactness, portability, blandness of taste, and ease of administration). Although tablets are most frequently discoid in shape, they may also be round, oval, oblong, cylindrical, rectangular or triangular, for example. The tablets may be optionally scored so that they may be separated into different dosages. They may differ greatly in size and weight depending on the amount of the pharmaceutically acceptable active agent or agents present and the intended route of administration. They are divided into two general classes, (1) compressed tablets, and (2) molded tablets.

Tablets and other orally discrete dosage forms, such as capsules, cachets, pills, granules, pellets, beads, and particles, for example, may optionally be coated with one or more enteric coatings, seal coatings, film coatings, barrier coatings, compress coatings, fast disintegrating coatings, or enzyme degradable coatings for example. Multiple coatings may be applied for desired performance. Further, dosage forms may be designed for, by non-limiting example, immediate release, pulsatile release, controlled release, extended release, delayed release, targeted release, synchronized release, or targeted delayed release. For release/absorption control, carriers may be made of various component types and levels or thicknesses of coats. Such diverse carriers may be blended in a dosage form to achieve a desired performance. In addition, the dosage form release profile may be effected by a polymeric matrix composition, a coated matrix composition, a multi-particulate composition, a coated multi-particulate composition, an ion-exchange resin-based composition, an osmosis-based composition, or a biodegradable polymeric composition.

While manufacture of implementations of an N-acetyl beta alanine composition or compound have been described in particular sequences of steps and/or in particular forms, it will be understood that such manufacture is not limited to the specific order of steps or forms as disclosed. Any steps or sequences of steps of manufacture of implementations of an N-acetyl beta alanine composition or compound in any form are given as examples of possible steps or sequences of steps or potential forms and not as limitations, since many possible manufacturing processes and sequences of steps may be used to manufacture N-acetyl beta alanine composition or compound implementations in a wide variety of forms.

Use

Implementations of an N-acetyl beta alanine Compound or Composition are particularly useful as supplements to increase athletic/sports/muscle performance in humans and animals, however, it can be used for any other use. However, implementations are not limited to these uses. Rather, any description relating to the foregoing is for the exemplary purposes of this disclosure. It will be understood that implementations of an N-acetyl beta alanine Compound or Composition may encompass a variety of uses for which beta-alanine is typically administered, such as muscle and overall health, anti-aging, nervous system health, etc.

Thus, in one aspect, a method is disclosed for enhancing athletic performance. The method includes administering a pharmaceutically effective amount to a human or animal of n-acetyl beta alanine.

In another aspect, a method is disclosed for preventing paresthesia. The method includes administering a pharmaceutically effective amount to a human or animal of n-acetyl beta alanine.

The N-acetyl form of beta alanine cannot react with nerve ends to produce paresthesia since amides are neurologically inactive. Therefore, by slowly converting to beta-alanine through deacetylation, paresthesia is prevented due to low but constant blood-serum beta alanine concentrations. This also increases the half-life of beta-alanine present in the blood stream and cell membrane permeability.

For the exemplary purposes of this disclosure, the Applicants have administered N-acetyl beta alanine to over 30 different subjects in doses ranging from 1 to even 10 grams. No paresthesia or negative feelings were described by any of the users. The paresthesia-preventing property of N-acetyl beta alanine is easy to prove—anyone can try to ingest 5 grams of beta-alanine and after the paresthesia has subsided consume 5 grams of n-acetyl-beta alanine and observe that no paresthesia takes place.

For the exemplary purposes of this disclosure, the Applicants have also administered N-acetyl-beta alanine at a dose of 5 grams per day ×1 in 10 subjects, all of them well trained athletes that had in the past used beta alanine and were well aware of it's benefits. All of the subjects had not used beta alanine for at least a month. They were asked to report the effects of the "new beta alanine preparation" they were offered. They all reported that N-acetyl-beta alanine resulted in improved effectiveness over normal beta-alanine and also that the full benefits were exhibited at a faster rate.

Based on these initial studies, the Applicants have moved forward with a major University to organize a study that will compare N-acetyl beta-alanine's effectiveness over beta-alanine's effectiveness.

As additional support, studies showing effectiveness for muscle performance and the like are as follows.

In "Role of beta-alanine supplementation on muscle carnosine and exercise performance", Artioli et al., Med Sci Sports Exerc. 2010 June; 42(6):1162-73, studies on beta alanine supplementation and exercise performance have demonstrated improvements in performance during multiple bouts of high-intensity exercise and in single bouts of exercise lasting more than 60 s. Similarly, beta alanine supplementation has been shown to delay the onset of neuromuscular fatigue. Although beta alanine does not improve maximal strength or VO2max, some aspects of endurance performance, such as anaerobic threshold and time to exhaustion, can be enhanced. Symptoms of paresthesia may be observed if a single dose higher than 800 mg is ingested.

In "Muscle carnosine metabolism and beta-alanine supplementation in relation to exercise and training", Derave et al., Sports Med. 2010 Mar. 1; 40(3):247-63 it explains that beta alanine is rapidly developing as a popular ergogenic nutritional supplement for athletes worldwide, and the currently available scientific literature suggests that its use is evidence based. However, many aspects of the supplement, such as the potential side effects and the mechanism of action, require additional and thorough investigation by the sports science community.

In "Beta-alanine supplementation reduces acidosis but not oxygen uptake response during high-intensity cycling exercise", Baquet et al., Eur J Appl Physiol. 2010 February; 108 (3):495-503, results indicate that chronic beta-alanine supplementation, which presumably increased muscle carnosine content, can attenuate the fall in blood pH during high-intensity exercise. This may contribute to the ergogenic effect of the supplement found in some exercise modes.

In "Effect of beta-alanine supplementation on the onset of blood lactate accumulation (OBLA) during treadmill running: Pre/post 2 treatment experimental design", Jordan et al., Journal of the International Society of Sports Nutrition 2010, 7:20, it was demonstrated that beta alanine supplementation for 28 days enhanced sub-maximal endurance performance by delaying OBLA. However, βA supplemented individuals had a reduced aerobic capacity as evidenced by the decrease in $VO_{2max}$ values post supplementation.

In "Beta-alanine and the hormonal response to exercise", Hoffman et al., Int J Sports Med. 2008 December; 29(12): 952-8, results indicate that four weeks of beta alanine supplementation can significantly improve muscular endurance during resistance training in experienced resistance-trained athletes. However, these performance gains did not affect the acute endocrine response to the exercise stimulus.

In "The effects of 10 weeks of resistance training combined with beta-alanine supplementation on whole body strength, force production, muscular endurance and body composition", Kendrick et al., Amino Acids. 2008 May; 34(4):547-54, subjects were assessed prior to and after training for whole body strength, isokinetic force production, muscular endurance, and body composition. Beta alanine supplemented subjects increased Muscle-Carnosine by 12.81+/−7.97 mmol×kg (−1) dry muscle whilst there was no change in Placebo Group subjects.

As further support, one study showing effectiveness for mood improvement through dopamine increase and anxiolytic effects and the like is "The impact of taurine- and beta-alanine-supplemented diets on behavioral and neurochemical parameters in mice: antidepressant versus anxiolytic-like effects", Murakami et al., Amino Acids. 2010 July; 39(2):427-34, where results suggest that taurine-supplemented diet had an antidepressant-like effect and beta-alanine-supplemented diet had an anxiolytic-like effect.

As even further support, studies showing effectiveness for Antiaging/Geriatric effects and the like are the following:

In "The effect of beta-alanine supplementation on neuromuscular fatigue in elderly (55-92 Years): a double-blind randomized study", Stout et al., Journal of the International Society of Sports Nutrition 2008, 5:21, findings suggest that ninety days of beta alanine supplementation may increase physical working capacity by delaying the onset of neuromuscular fatigue in elderly men and women.

In "Carnosine and Its Possible Roles in Nutrition and Health", Hipkiss, Advances in Food and Nutrition Research, Volume 57, 2009, Pages 87-154, evidence for carnosine's possible protective action against secondary diabetic complications, neurodegeneration, cancer, and other age-related pathologies is briefly discussed.

In "Possible new antiaging strategies related to neuroendocrine-immune interactions", Mocchegiani et al., Neuroimmunomodulation. 2008; 15(4-6):344-50, discloses some substances which can be proposed as new antiaging strategies because of their capacity to remodel some biological functions in old animals and humans. Among them is carnosine It's role as possible antiaging strategy in healthy people in relation to neuroendocrine-immune responses and zinc ion bioavailability is reported and discussed.

In "Carnosine, the anti-ageing, anti-oxidant dipeptide, may react with protein carbonyl groups" Hipkiss, Mechanisms of Ageing and Development, Volume 122, Issue 13, 15 Sep. 2001, Pages 1431-1445, a preliminary experiment suggests that carnosine is effective in vivo; it suppressed diabetes-associated increase in blood pressure in fructose-fed rats, an observation consistent with carnosine's anti-glycating actions. Researchers speculate that: (i) carnosine's apparent anti-ageing actions result, partly, from its ability to react with carbonyl groups on glycated/oxidised proteins and other molecules; (ii) this reaction, termed 'carnosinylation,' inhibits cross-linking of glycoxidised proteins to normal macromolecules; and (iii) carnosinylation could affect the fate of glycoxidised polypeptides.

The invention claimed is:

1. A method for increasing athletic performance in a human without causing paresthesia, the method comprising administering to the human an effective amount of N-Acetyl Beta Alanine.

* * * * *